US005298222A

United States Patent [19]

O'Leary

[11] Patent Number: 5,298,222
[45] Date of Patent: Mar. 29, 1994

[54] PROCESS FOR DISINFECTING MUSCULOSKELETAL TISSUE AND TISSUES PREPARED THEREBY

[75] Inventor: Robert K. O'Leary, Spring Lake, N.J.

[73] Assignee: Osteotech, Inc., Shrewsbury, N.J.

[21] Appl. No.: 391,233

[22] Filed: Aug. 9, 1989

[51] Int. Cl.$^5$ ............................................. A61L 2/18
[52] U.S. Cl. ...................................... 422/28; 422/40; 424/549; 424/684; 435/1
[58] Field of Search ............... 436/174, 175, 176, 177, 436/825; 424/684, 549; 422/28, 40; 435/1

[56] References Cited

U.S. PATENT DOCUMENTS

| | | | |
|---|---|---|---|
| 3,126,884 | 3/1964 | Tucker, Jr. | 422/549 |
| 4,277,238 | 7/1981 | Katagiri | 422/36 X |
| 4,379,143 | 4/1983 | Sherry et al. | 424/684 |

FOREIGN PATENT DOCUMENTS

| | | |
|---|---|---|
| 582001 | 11/1976 | Switzerland . |
| 8401894 | 5/1984 | World Int. Prop. O. . |
| 8803411 | 5/1988 | World Int. Prop. O. . |

*Primary Examiner*—Jill A. Johnston
*Attorney, Agent, or Firm*—Elliot M. Olstein; Raymond J. Lillie; Susan A. Capello

[57] ABSTRACT

A process for treating musculoskeletal tissue which comprises contacting musculoskeletal tissue with both an effective amount of at least one treating agent selected from the class consisting of antibiotics and disinfectants, and an agent to increase diffusion of the treating agent into the tissue, such as a surfactant or a permeation enhancer. The disinfectant and/or antibiotic function in killing bacteria, vegetative organisms, and viruses (including HIV virus) which may be remaining in the musculoskeletal tissue. A preferred disinfectant is ethanol.

13 Claims, No Drawings

PROCESS FOR DISINFECTING MUSCULOSKELETAL TISSUE AND TISSUES PREPARED THEREBY

This invention relates to the processing of musculoskeletal tissue for use in grafts and transplants. More particularly, this invention relates to a process for preparing and disinfecting musculoskeletal tissue under sterile conditions, employing disinfectant and/or antibiotic, whereby there is improved penetration and diffusion of the antibiotic or disinfectant or sterilizing medium into the musculoskeletal tissue.

In general, in processing musculoskeletal tissue for use in grafts and transplants, the musculoskeletal tissue, which may include, in addition to bone, connective tissue, such as fascia, tendons, ligaments, etc., is removed from the body under sterile conditions. The tissue is then soaked in an antibiotic and then wrapped under sterile conditions for transport to facilities for further processing.

Once the tissue is ready to be processed further, it is unwrapped under sterile conditions and, in the case of bone, then debrided; i.e., connective tissue and periosteum are removed from the bone. After debridement, the bone is shaped under sterile conditions into a specific size meeting formal specifications for surgical requirements.

After the bone has been shaped, it is treated with a disinfectant in order to kill vegetative organisms. After treatment with the disinfectant, the bone is then washed with sterile water and packaged under sterile conditions. Such tissue may be frozen until it is ready for use.

It is an object of the present invention to provide a process whereby there is achieved improved penetration, diffusion, permeation, solubility, and sorption of an antibiotic and/or disinfectant into musculoskeletal tissue during the preparation of such tissue for grafts and transplants.

In accordance with an aspect of the present invention, there is provided a process for treating musculoskeletal tissue which comprises contacting musculoskeletal tissue with both an effective amount of at least one treating agent selected from the class consisting of antibiotics and disinfectants and an agent to increase diffusion of the at least one treating agent into the tissue which agent is preferably a surfactant or a permeation enhancer.

The antibiotics which may be employed in accordance with the present invention are generally present in an aqueous solution. One or a combination of antibiotics may be used to treat the musculoskeletal tissue in accordance with the present invention. Antibiotics which may be employed include bacitracin, polymyxin B sulfate, erythromycin, neomycin, penicillin, tetracyclines, viomycin, chloromycetin, streptomycins, cefazolin, ampicillin, tobramycin, clindamycin, and gentamicin. The antibiotic(s) is employed in an effective antibiotic amount. The term "antibiotic" as used herein means that the antibiotics produce effects adverse to the normal biological functions of organisms within the musculoskeletal tissue, including death or destruction or prevention of the growth of such organisms.

The disinfectants which may be employed in accordance with the present invention are generally present in an aqueous solution, and are administered in an effective disinfecting amount. Examples of disinfectants which may be employed within the scope of the present invention include ethylene oxide, propylene oxide, ethanol, hydrogen peroxide (preferably as 10% hydrogen peroxide in aqueous solution), chlorine dioxide, chlorahexidene gluconate, glutaraldehyde, formaldehyde, peracetic acid (hydrogen peroxide and acetic acid in aqueous solution), povadone iodide (polyvinylpyrollidone), sodium hypochlorite, quaternary ammonium compounds cetyl alcohol and benzalkonium chloride. A preferred disinfectant is an aqueous ethanol solution.

The disinfectants employed within the scope of the present invention will kill vegetative organisms, which may be remaining in the musculoskeletal tissue. In addition, the disinfectants may also act as a viricide and kill viruses within the musculoskeletal tissue as well. Ethanol, for example, has a viricidal effect upon a variety of viruses, including HIV, or AIDS, virus. Ethanol also functions in removing any fat which remains in the tissue.

It is to be understood that within the scope of the present invention, antibiotic(s) alone, disinfectant(s) alone, or a combination of antibiotic(s) and disinfectant(s) may be used in combination with the agent to increase diffusion of the treating agent(s) into the tissue.

The agent for increasing diffusion of the treating agent into the tissue is preferably a surfactant or a permeation enhancer. The surfactant employed in accordance with the present invention may be a cationic, non-ionic, anionic, or amphoteric surfactant. The surfactant should be a biocompatible surfactant and miscible with the disinfectant, such as ethanol, or with the antibiotic.

Cationic surfactants which may be employed include quaternary amino or nitrogen compounds; quaternary ammonium salts such as benzalkonium chloride, alkyltrimethylammonium salts, and alkylpyridinium salts; aliphatic mono-,di-, and polyamines; rosin-derived amines; amine oxides, such as polyoxyethylene alkyl and alicyclic amines, N, N, N, N tetrakis-substituted ethylene diamines, amide-linked amines, preferably those prepared by the condensation of a carboxylic acid with a di-or polyamine, and sodium tauro-24, 25-dihydrofusidate.

Anionic surfactants which may be employed include sulfates such as alkyl sulfates (for example, sodium dodecyl sulfate), sulfated fats and oils, sulfated oleic acid, sulfated alkanolamides, sulfated esters, and alcohol sulfates; sulfonates such as alkylaryl sulfonates, olefin sulfonates, ethoxylated alcohol sulfates, and sulfonates of ethoxylated alkyl phenols; sulfates of fatty esters; sulfates and sulfonates of alkyl phenols; lignosulfonates; sulfonates of condensed naphthalenes; sulfonates of naphthalene; dialkyl sulfosuccinates, preferably sodium derivatives; sodium derivatives of sulfo-succinates, such as the disodium ethoxylated nonyl phenol half ester of sulfosuccinic acid, the disodium ethoxylated alcohol ($C_{10}$-$C_{11}$), half-ester of sulfosuccinic acids, etc., petroleum sulfonates, such as alkali salts of petroleum sulfonates; for example, sodium petroleum sulfonate (Acto 632); phosphate esters, such as alkali phosphate esters, and a potassium salt of phosphate ester (Triton H66); sulfonated alkyl esters (for example, Triton GR 7); carboxylates, such as those of the formula (RCOO)-(M)+ wherein R is an alkyl group having from 9–21 carbon atoms, and M is a metal or an amine; and sodium polymeric carboxylic acid (Tamol 731) and the like.

Nonionic surfactants which may be employed include polyoxyethylenes; ethoxylated alkyl phenols, ethoxylated aliphatic alcohols; carboxylic acid esters, such as glycerol esters, polyethylene glycol esters, and polyoxyethylene fatty acid esters; anhydrosorbitol esters and ethoxylated anhydrosorbitol esters; glycol esters of fatty acids; ethoxylated natural fats, oils, and waxes; carboxylic amides, such as diethanolamine condensates, and monoalkanolamine condensates; polyoxyethylene fatty acid amides; polyalkylene oxide block copolymers, preferably polyethylene and polypropylene oxide block copolymers; and polysiloxane-polyoxyalkylene copolymers; 1-dodecylazacycloheptan-2-one (Nelson R & D); polyethylene glycol monolaurate (Alza); and Macrochem's SEPA nonionic surfactant.

Preferred non-ionic surfactants are non-ionic surfactants which are ethylene oxide condensation products (polyoxyethylene) containing more than two, and preferably at least five ethylene oxide groups, with at least one end group thereof being terminated by condensation with either an alcohol, alkylphenol, or a long chain fatty acid. A particularly preferred non-ionic surfactant is an octylphenoxy polyethoxyethanol surfactant known as Triton X-100.

Amphoteric surfactants include N-coco-3 aminopropionic acid and its sodium salt; disodium salts of N-tallow-3-iminodipropionate and N-lauryl-3-iminodipropionate; N-carboxymethyl-N cocoalkyl-N-dimethylammonium hydroxide; N-carboxymethyl-N-dimethyl-N-(9-octadecenyl) ammonium hydroxide; (1-carboxy heptadecyl) trimethylammonium hydroxide; (1-carboxyundecyl) trimethylammonium hydroxide; sodium salts of N-cocoamidoethyl-N-hydroxyethylglycine and N-hydroxyethyl-N-stearamido-glycine; sodium salts of N-hydroxyethyl-N-lauramido-B-alanine and N-cocoamido-N-hydroxyethyl-B-alanine; sodium salts of mixed alicyilic amines, ethoxylated and sulfated sodium salts or free acids of 2-alkyl-1 carboxymethyl-1-hydroxyethyl-2-imidazolinium hydroxide; the disodium salt of 1, 1-bis (carboxymethyl)-2-undecyl-2-imidazolinium hydroxide; and the sodium salt of a propoxylated and sulfated oleic acid-ethylenediamine condensate.

In lieu of a surfactant, it is to be understood that a permeation enhancer may be employed as the agent to increase diffusion of the at least one treating agent (disinfectant and/or antibiotic) into the musculoskeletal tissue. The term "permeation enhancer" as used in the art and herein means an agent which aids or assists a material (e.g., a drug) to dissolve into and diffuse through the skin. Applicant has found that such permeation enhancers may be employed to increase diffusion of a treating agent into musculoskeletal tissue.

Permeation enhancers which may be employed within the scope of the present invention include glycerol monolaurate; hexamethylene lauramide; dimethyl formamide; propylene glycol; diethyltoluamide; N-methyl-2-pyrrolidone; decylmethylsulfoxide; benzyl alcohol; dimethyl sulfoxide; alkyl-N-N-dialkyl-substituted amino acetates; lecithin; dimethylacetamide; laurocapram; dodecyl-L-pyroglutamate; 1-oxohydrocarbyl-substituted azacyclohexanes; azone; hydroxyethyl acetamide; tetrahydrofurfuryl alcohol; methyl laurate; isopropyl palmitate; isopropyl myristate; and isopropyl stearate. Preferred permeation enhancers are isopropyl palmitate and isopropyl myristate. it is to be understood, however, that the scope of the present invention is not to be limited to the specific permeation enhancers hereinabove described.

The disinfectant is employed alone or in an aqueous solution. Preferably, the disinfectant is added in an aqueous solution in an amount of from about 1% to about 100% by volume. The agent to increase diffusion of the treating agent into the tissue, such as a surfactant or permeation enhancer, is added in an amount effective to increase diffusion of the disinfectant into the tissue. The agent is preferably added to an aqueous solution of the disinfectant in an amount of from about 0.0001% to about 10% of the resulting aqueous solution, preferably from about 0.01% to about 10% by volume. Wherein an antibiotic is included as a treating agent, the antibiotic(s) is preferably added in an aqueous solution, in an amount amount of from about 30,000 units to about 50,000 units, and the agent to increase diffusion of the treating agent (i.e., the antibiotic) into the tissue, such as a surfactant or permeation enhancer, is added to the aqueous solution in an amount of from about 0.0001% to about 10% of the resulting aqueous solution, preferably from about 0.01% to about 10% by volume. The combination of disinfectant or antibiotic(s) and surfactant or permeation enhancer is preferably applied to the tissue as an aqueous mixture.

Although the present invention is not intended to be limited to any theoretical reasoning, it is believed that, when a surfactant is employed as the agent to increase diffusion of the treating agent into the tissue, the combination of disinfectant and/or antibiotic and surfactant alters the surface tension of the cells of the musculoskeletal tissue, thereby providing for improved or enhanced penetration of the disinfectant or antibiotic into and diffusion of the disinfectant or antibiotic through the tissue. The improved absorption of the disinfectant or antibiotic into the tissue provides for increased killing of bacteria, vegetative organisms, and/or viruses which may be remaining in the musculoskeletal tissue. In addition, the use of a surfactant can provide viricidal activity in that surfactants can function to disrupt viruses.

When a permeation enhancer is employed as the agent to increase diffusion of the treating agent into the tissue, it is believed that the permeation enhancer increases the solubility of the antibiotic and/or disinfectant; i.e., the permeation enhancer increases the ability of the antibiotic and/or disinfectant to dissolve into the musculoskeletal tissue. It is also believed that the permeation enhancer increases the diffusion, or rate of movement, of the antibiotic and/or disinfectant through the tissue.

Tissue which may be disinfected in accordance with the present invention includes bone tissue, and connective tissue such as tendons, fascia, and ligaments. Specific examples of musculoskeletal tissue which may be prepared for use in grafts or transplants in accordance with the present invention include cortical/cancellous tissue, cancellous chips, cloward dowels, iliac crest wedges, ilium bicortical strips, ilium tricortical strips, cortical strips, bone-tendon-bone (patellar) grafts, achilles tendon (which may also include a calcaneous), fascia lata, proximal tibia, distal femur, proximal humerus, (with or without rotator cuff), proximal femur, whole knee, whole femur, fibula, ribs, femoral heads, fibular shafts, femoral shafts, and tibial shafts.

In accordance with another aspect of the present invention, there is provided a product comprising tissue prepared by the process hereinabove described.

It is to be understood, however, that the scope of the present invention is not to be limited to the specific embodiments described above. The invention may be practiced other than as particularly described and still be within the scope of the accompanying claims.

What is claimed is:

1. A process for treating bone with both an effective amount of at least one treating agent selected from the class consisting of antibiotics and disinfectants, and an agent to increase diffusion of the treating agent into the bone, said agent being selected from the group consisting of surfactants and permeation enhancers.

2. The process of claim 1 wherein the treating agent is at lest one antibiotic.

3. The process of claim 2 wherein said at least one antibiotic is added in an amount of from about 30,000 units to about 50,000 units.

4. The process of claim 1 wherein the treating agent is at least one disinfectant.

5. The process of claim 4 wherein said at least one disinfectant is an aqueous ethanol solution.

6. The process of claim 4 wherein said at least one disinfectant is added in an aqueous solution in an amount of from about 1% to about 100% by volume.

7. The process of claim 1 wherein said agent to increase diffusion of the treating agent into the bone is a surfactant.

8. The process of claim 7 wherein the surfactant is a non-ionic surfactant.

9. The process of claim 7 wherein the surfactant is miscible with said at least one treating agent.

10. The process of claim 1 wherein said agent to increase diffusion of the treating agent into the bone is a permeation enhancer.

11. The process of claim 1 wherein said at least one treating agent and said agent to increase diffusion of the treating agent into the bone are applied as an aqueous mixture.

12. The process of claim 1 wherein the agent to increase diffusion of the treating agent into the bone is added in an aqueous solution in an amount of from about 0.0001% to about 10% by volume.

13. The process of claim 12 wherein the agent to increase diffusion of the treating agent into the bone is added in an amount of from about 0.01% to about 10% by volume.

* * * * *